United States Patent [19]

Shibuya et al.

[11] 4,305,956
[45] Dec. 15, 1981

[54] MITICIDAL METHOD

[75] Inventors: Hajime Shibuya; Yukio Inoue, both of Tokyo; Shiro Okuda, Saitama; Makoto Hattori, Jyoetsu, all of Japan

[73] Assignee: Kaken Chemical Co., Ltd., Tokyo, Japan

[21] Appl. No.: 150,149

[22] Filed: May 15, 1980

[51] Int. Cl.$^3$ .............................................. A01N 43/16
[52] U.S. Cl. .................................................. 424/283
[58] Field of Search ........................................ 424/283

[56] References Cited

U.S. PATENT DOCUMENTS 4,033,823 7/1977 Liu et al. ........................ 435/118
4,066,781 1/1978 Shibuya et al. ................. 424/283

*Primary Examiner*—Leonard Schenkman
*Attorney, Agent, or Firm*—Oblon, Fisher, Spivak, McClelland & Maier

[57] ABSTRACT

A miticidal method comprises applying a miticidal composition comprising Lysocellin having the formula

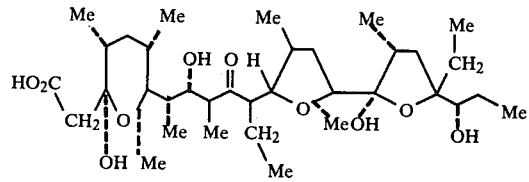

or its salt or ester.

3 Claims, No Drawings

MITICIDAL METHOD

BACKGROUND OF THE INVENTION

1. Field of the Invention

The present invention relates to novel miticidal compositions.

2. Description of the Prior Arts

Parasitic mites such as citrus red mite and two-spotted mite cause damages to fruit trees and vegetables. Various miticides have been studied and practically applied for inhibiting such parasitic mites. Most of these miticides have been effective even though they are applied at high concentration because of resistance of parasitic mites.

In order to overcome such resistance of parasitic mites, a continuous application of the same type miticides is prevented and great efforts have been made for a development of novel miticides.

The inventors have found that the antibiotic Salinomycins have strong miticidal effect to control imagines, larvae and ova of mites.

The inventors have further studied miticidal effects of novel type compounds in various groups. As a result, certain antibiotic has excellent miticidal effect.

SUMMARY OF THE INVENTION

It is an object of the present invention to provide a miticidal composition which is remarkably effective for controlling parasitic mites without resistance of the mites.

The foregoing and other objects of the present invention have been attained by providing a miticidal composition comprising Lysocellin having the formula

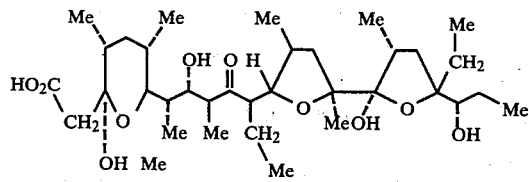

or its salt or ester as an active ingredient.

DETAILED DESCRIPTION OF THE PREFERRED EMBODIMENTS

The inventors have found that Lysocellins, (including its salts or esters) are effective for controlling various plant parasitic mites and the mechanism for controlling the plant parasitic mites has a special characteristic.

It has been found that Lysocellins are effective for controlling imagines, larvae and ova of mites as the conventional miticides and for preventing ecdysis of larvae to cause mortality and for sterility by a treatment with a dilute concentration remarkably lower than the usual concentration for mortality.

The present invention has been attained by said finding to provide a miticidal composition comprising Lysocellin, its salt or ester as an active ingredient.

Lysocellin is an antibiotic having excellent antibial activity which is isolated from a fungus body and medium which is cultured from Streptomyces and has the formula

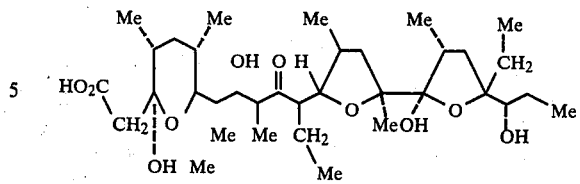

The active ingredient of the miticidal composition of the present invention can be Lysocellin in free form, or its carboxylic salts such as sodium, potassium, calcium, magnesium or ammonium salt or its esters for hydroxyl group at 21-position, preferably acetyl ester. Two or more active ingredients can be also used.

The parasitic mites which are controlled by the miticidal composition of the present invention include plant parasitic mites, spider mites such as citrus red mite, European red mite, Kanzawa spider mite, two-spotted spider mite, carmine mite, sweet cherry spider mite, clover mite, Sugi spider mite, sourthern red mite, Smith spider mite and rust mite, red mite, root mite, and animal parasitic mites such as house mite, rickettsia orientalis, hair mite, powder mite and dust mite, etc.

The miticidal compositions of the present invention can be in the form of an emulsifiable concentrate, a suspension, an aqueous solution, a wettable powder, a dust, an oily solution, an aerosol smoking composition. These miticidal compositions can be prepared by desired methods. The carriers can be natural or synthetic organic or inorganic compounds. Suitable solid carriers include inorganic carriers such as clay, talc, mica, agalmatolite, vermiculite, gypsum, calcium carbonate, diatomaceous earth, zeolite, bentonite, fine silica and anhydrous silica; organic carriers such as saw dust, wheat powder, soybean powder, starch, alkyd resin, polyvinyl chloride, ester rubber and urea. Suitable liquid carriers include water, ketones, alcohols, esters, ethers, aromatic and aliphatic hydrocarbons, chlorinated hydrocarbons, and polar solvents such as dimethylformamide and dimethylsulfoxide.

It is possible to incorporate a nonionic, anionic, cationic or ampholytic surfactants with said carrier depending upon the form, for a purpose of an emulsification, a dispersion or a wetting.

The miticidal composition of the present invention can be used together with the other ingredient such as fungicides, insecticides, herbicides, plant growth regulator, other miticides, fertilizers, external preparations for animals repellents, etc.

The miticidal compositions of the present invention are applied by a soil treatment, a foliage application, a spray application in animal cages and fowls cages, and coating on external part of an animal etc. at suitable ages of larvae, ova and imagines of mites depending upon the purpose of the application.

Suitable dose of the active ingredient of Lysocellin (including its salt or ester) is depending upon the object mites and applications and is usually in a range of 1 to 1000 g. preferably 10 to 100 g. of Lysocellin per 10 ares in the foliage treatment. The purpose can be attained with the similar does in the spray application in animal cages and fowls cages.

Lysocellin (including its salt or ester) can exhibit remarkable miticidal effect as shown in the following experiments and is usually applied as the miticidal compositions. Typical examples of miticidal compositions are illustrated.

Composition 1:

A dust was prepared by mixing 0.1 wt. part of Lysocellin, 5 wt. parts of fine silica, 30 wt. parts of clay and 64.9 wt. parts of talc and pulverizing the mixture.

Composition 2:

A wettable powder was prepared by mixing 2 wt. parts of Lysocellin, 10 wt. parts of fine silica, 50 wt. parts of clay, 35 wt. parts of diatomaceous earth and 3 wt. parts of an emulsifier (Sorpol 4048: Toho Chem.), and pulverizing the mixture. In the application, the wettable powder is diluted with water for the spray.

Composition 3:

An emulsifiable concentrate was prepared by uniformly mixing 20 wt. parts of Lysocellin, 20 wt. parts of isopropanol, 55 wt. parts of xylol and 5 wt. parts of an emulsifier (Sorpol 2680: Toho Chem.) to dissolve Lysocellin. In the application, the emulsifiable concentrate is diluted with water for the spray.

EXPERIMENT 1

Effect on imago of mites:

Kidney bean seedlings were cultured in a pot having a diameter of about 6 cm.

About 30 female imagines of carmine mites (Tetranychus tetrarus) were positioned on primary leaves at two leaf stage (two days after germination). One day later, the damaged mites were removed and the primary leaves were dipped into each solution obtained by diluting the emulsifiable concentrate of Composition 3 with water at a concentration of the active ingredient shown in Table 1, for 10 seconds. Two days after the treatment with the composition, each mortality of the imagines of the mite was measured. The results are shown in Table 1.

TABLE 1

| Concentration of Lysocellin (ppm) | Mortality of imagines (%) |
| --- | --- |
| 10 | 59 |
| 100 | 73 |
| 500 | 100 |

EXPERIMENT 2

Effect on ova and larvae of mites:

About 30 to 40 ova were ovipositioned by imagines of carmine mites, on primary leaves of kidney bean at two leaf stage (two days after germination). The imagines were removed. The primary leaves were dipped into each solution obtained by diluting the emulsifiable concentrate of Cmposition 3, with water at a concentration of the active ingredient shown in Table 2, for 10 seconds. Eight days after the treatment with the composition, each mortality of the ova and larvae were measured. The results are shown in Table 2. The mortality of the larvae is considered to be caused by the ecdysis inhibition of Lysocellin.

TABLE 2

| Concentration of Lysocellin (ppm) | Mortality (%) | |
| --- | --- | --- |
| | Ova | Larvae |
| 0 | 0 | 0 |
| 50 | 90.9 | 100 |
| 100 | 98.1 | 100 |
| 200 | 100 | 100 |

EXPERIMENT 3

Effect on larvae of mites:

In accordance with the test of Experiment 3, the oviposition was resulted after six days from the position, the primary leaves with the larvae were dipped into a solution containing Lysocellin at the specific content of 10 seconds. Ten days after the treatment, with the composition, each mortality of larvae was measured. The results are shown in Table 3.

TABLE 3:

| Concentration of Lysocellin (ppm) | Mortality of larvae (%) |
| --- | --- |
| 5 | 100 |
| 10 | 100 |
| 20 | 100 |

EXPERIMENT 4

Effect on sterility of female imagines of mites:

In accordance with the process of Experiment 1, 10 female imagines of carmine mites were positioned on primary leaves of kidney bean and the primary leaves were dipped into each solution having each desired concentration of the active ingredient for 10 seconds. Ten days after the treatment with the composition, the mortality was measured. The results are shown in Table 4.

TABLE 4

| Concentration of Lysocellin (ppm) | Mortality (%) |
| --- | --- |
| 0 | 0 |
| 2.5 | 52.6 |
| 3.75 | 76.9 |
| 5.0 | 66.7 |
| 7.5 | 94.1 |
| 10 | 100 |

EXPERIMENT 5

Persistence:

The primary leaf of kidney bean of Experiment 1 was dipped into each solution containing Lysocellin at the specific content, for 10 seconds and dried at the ambient temperature. After the treatment, 10 female imagines of carmine mites were positioned on each treated cotyledon to result the oviposition for 3 days, and the mortality was measured five days after the oviposition. The results are shown in Table 5.

| Oviposition | Concentration of Lysocellin (ppm) | Mortality (%) | |
| --- | --- | --- | --- |
| | | Ova | Imagines |
| Dipped day | 10 | 65.5 | 100 |
| Dipped day | 100 | 86.7 | 100 |
| 3 days after dip. | 10 | 27.9 | 100 |
| 3 days after dip. | 100 | 93.0 | 100 |
| 7 days after dip. | 10 | 68.1 | 82.5 |
| 7 days after dip. | 100 | 78.3 | 95.5 |

We claim:

1. A miticidal method which comprises applying a miticidal composition comprising Lysocellin having the formula:

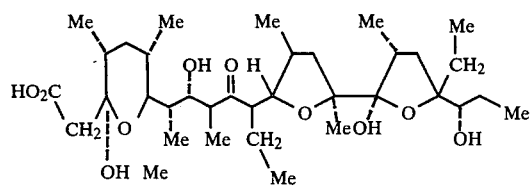
or its salt or its ester for the hydroxyl group at 21 position to imagines, larvae or ova of mites at a dose of 1 to 1000 g. per 10 acres.
2. The method of claim 1 wherein said salt is sodium, potassium, calcium, magnesium or ammonium.
3. The method of claim 2 wherein said ester is acetyl ester.
* * * * *